United States Patent [19]

Salter et al.

[11] 4,106,505
[45] Aug. 15, 1978

[54] NASAL CANNULA ASSEMBLY

[75] Inventors: Peter W. Salter; William W. Cook, both of Arvin, Calif.

[73] Assignee: Salter Labs., Inc., Arvin, Calif.

[21] Appl. No.: 760,239

[22] Filed: Jan. 17, 1977

[51] Int. Cl.² .............................................. A61M 16/00
[52] U.S. Cl. .................................. 128/206; 128/348; 128/DIG. 26
[58] Field of Search ............... 128/206, 198, 207, 200, 128/199, 185, 147, 145.8, 348 R, 140 N, DIG. 9, DIG. 26

[56] References Cited

U.S. PATENT DOCUMENTS

| 1,486,290 | 3/1924 | Littauer | 128/206 |
|---|---|---|---|
| 2,763,263 | 9/1956 | Ellman | 128/198 |
| 2,868,199 | 1/1959 | Hudson | 128/206 |
| 3,754,552 | 8/1973 | King | 128/206 |

Primary Examiner—Robert W. Michell
Assistant Examiner—Henry J. Recla
Attorney, Agent, or Firm—Charles C. Logan, II

[57] ABSTRACT

A nasal cannula assembly designed for contact with the nasalabidial area of a patient's face comprising a nasal cannula, a pair of auxiliary oxygen supply tubes connected to the opposite ends of the nasal cannula, a slip loop disposed about the auxiliary supply tubes, and a main oxygen supply line. The nasal cannula is made of a flexible plastic material that is dip molded into a hollow tubular member having a main body portion whose cross-section is oval shaped with a vertical orientation and having a pair of spaced hollow tubular extensions projecting upwardly in a curved configuration from its upper surface. The main body portion has a horizontal axis extending along its length with an elbow formed at each end. An arm portion extends from each of the elbows and the axis of the arm portion intersects the horizontal plane of the axis of the main body portion at an acute angle from above the horizontal plane. The axis extending along the length of each arm also extends rearwardly at an acute angle to the horizontal axis of the main body portion. The acute angle at which the arm portion intersects the horizontal plane of the axis of the main body portion from above is such that the axis of the arm portion, if extended, will pass substantially tangential to the top of the patient's ear. The acute angle at which the arm portion extends rearwardly with respect to the horizontal axis of the main body portion is such that the axis, if extended, will pass substantially tangential to the top of the patient's ear. The arm portions have sleeve portions at their outer ends of reduced diameter for receiving the auxiliary supply tube.

8 Claims, 4 Drawing Figures

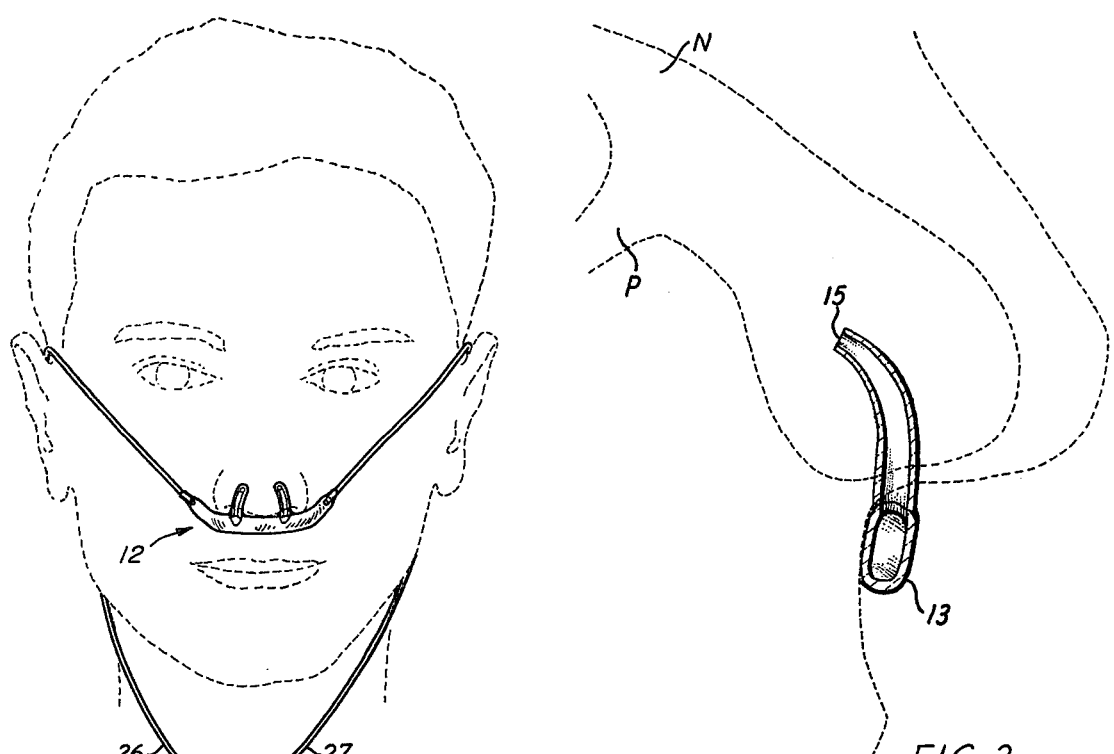
FIG. 3
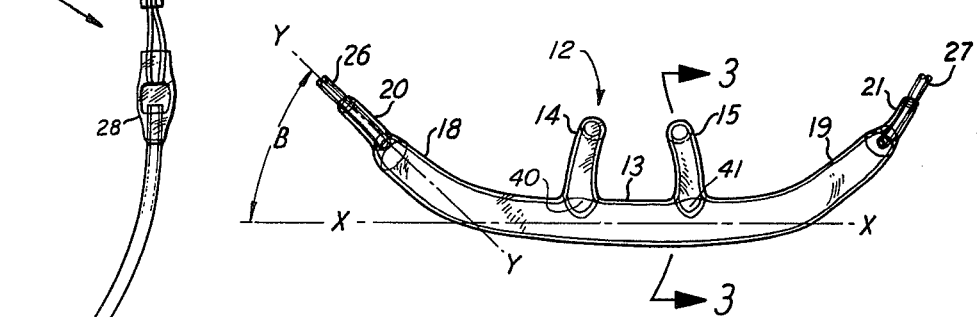
FIG. 2
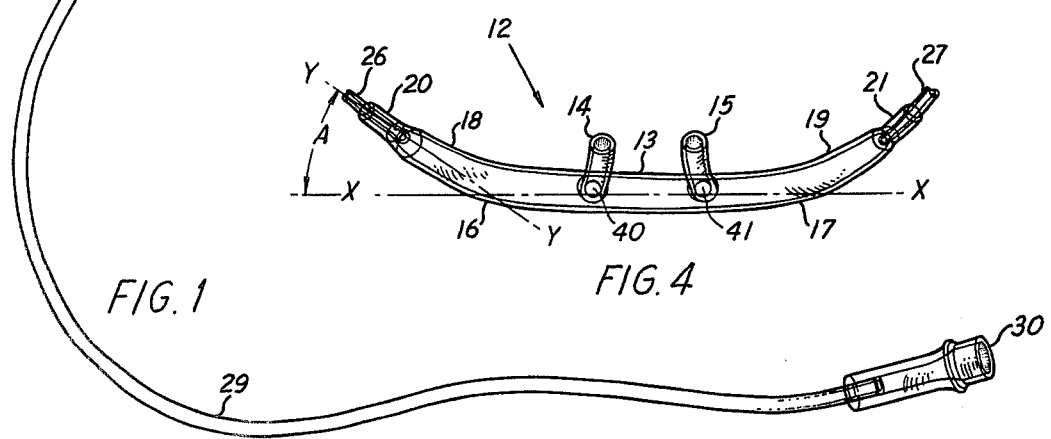
FIG. 1
FIG. 4

NASAL CANNULA ASSEMBLY

BACKGROUND OF THE INVENTION

The present invention relates to a nasal cannula assembly for use in the administration of fluids such as oxygen into the nasal passages of a person having respiratory ailments.

In the past, flexible cannulas have been produced that were positioned to contact the nasalabidial area between the patient's upper lip and nostrils (see U.S. Pat. Nos. 2,868,199 and 3,802,431). Even though these cannulas were made of soft, flexible plastic, the wearer encountered discomfort.

When a patient is required to have prolonged oxygen administration, it is necessary that the cannula be worn both during awakening hours as well as sleeping hours. This results in continued contact of the cannula especially at the philtrum and around the unprotected upper lip area causing irritation and inflamation. While the patient is talking or eating, rubbing contact occurs and even while sleeping, rubbing occurs as the patient inadvertently moves his head from side to side. As is the case in any instance of prolonged contact of a patient's skin with a foreign object, not only does irritation result, but inflamation and ulcerous conditions may occur after a period of time.

The contact problem in the nasalabidial area has also been compounded by the manner in which the cannula is held in position on the patient. Generally, the nasal extensions were inserted into the nostrils and an upward and rearward tension was applied to the cannula by the auxiliary oxygen supply tubes connected to the opposite ends of the cannula. These auxiliary supply tubes were pulled over the patient's ears and then looped downward and were cinched up relatively snugly by a slip loop passing around the two auxiliary supply tubes. In the absence of looping the supply tubes over the patient's ears, the weight of the cannula itself would cause the cannula to disengage itself from the nostrils and fall from the patient when his head was in an upright position. The pull of the auxiliary supply tubes caused pressure stresses where the cannula was pulled against the nasalabidial area.

Another prior cannula structure, (see U.S. Pat. No. 3,643,660), has been designed to eliminate contact in the nasalabidial area. Its shortcomings result from the fact that the lower edge of its flat upper surface bears against the upper nasalabidial area of the patient thereby creating an area susceptible to irritation and inflamation. This lower edge provides a relatively lengthy edge along which pressure is applied. Also, the auxiliary oxygen supply tubes extend outwardly from the cannula along the longitudinal axis of the cannula thereby requiring a pronounced tension on the supply tubes from around the top of the patient's ears again accentuating the pressure being applied against the patient's uppermost nasalabidial zone. The flat nature of the top surface of the cannula also increases the area of contact of the cannula with the anterior nares.

SUMMARY OF THE INVENTION

The novel nasal cannula assembly has been designed for contact with the nasalabidial area of a patient's face. It comprises a nasal cannula, a pair of auxiliary oxygen supply tubes connected to the opposite ends of the nasal cannula, a slip loop disposed about the auxiliary supply tubes, and a main oxygen supply line.

The nasal cannula is made of a flexible material such as polyvinylchloride that is dip molded into a hollow tubular member having a main body portion whose cross-section is oval shaped with a vertical orientation and having a pair of spaced, hollow tubular extensions projecting upwardly in a curved configuration from its upper surface. The tubular extensions are inserted into the nostrils of the wearer and the curved configuration permits a positive guiding of the oxygen supply along the natural contours of the nasal passages directly into the pharynx. The thin walls of the main body portion allows it to flatten against the nasalabidial area when subjected to minimal pressure and this provides a positive positioning of the nozzles within the nasal passage while spacing their lateral surfaces from the interior of the nasal passage.

The main body portion of the cannula has a horizontal axis extending along its length with an elbow formed at each end. An arm portion extends from each of the elbows and the axis of the arm portion intersects the horizontal plane of the axis of the main body portion at an acute angle from above the horizontal plane. The arm portions also have an oval shaped cross-section that is vertically oriented. The axis extending along the length of each arm also extends rearwardly at an acute angle to the horizontal axis of the main body portion. The acute angle at which the arm portion intersects the horizontal plane of the axis of the arm portion, if extended, will pass substantially tangential to the top of the patient's ear. The acute angle at which the arm portion extends rearwardly with respect to the horizontal axis of the main body portion is such that the axis, if extended, will pass substantially tangential to the top of the patient's ear. This novel structure allows the auxilliary supply tubes to be attached to the cannula in such a manner that a direct path is formed to the top of the patient's ears thus allowing a minimal tension in order to keep the cannula positioned against the nasalabidial area when the patient's head is in an upright position. This produces minimal pressure against the nasalabidial area and also against the back of the ear lobes. An additional benefit gained is the fact that the nasal cannula is held in place by the slight collapsing of the oval shaped main body portion as it is lightly pulled against the nasalabidial area in such a manner that the nasal extensions are prevented from rolling out of the nostrils.

The cannula is also sometimes positioned against the under surface of the nasal septum. The fact that the upper surface of the main body portion is rounded minimizes the area of contact on the nasal septum and also avoids any straight edges that would concentrate pressure against its contact point. The upward and inwardly configuration of the arm portions spreads the pressure of the weight of the cannula on the nasalabidial area when the patient is in a prone position. By spreading the surface contact over a larger area, the pressure is reduced upon any contact point. The rounded bottom surface of these arm portions also avoids any straight edges that would concentrate pressure against its contact point.

OBJECTS

It is an object of the invention to provide a nasal cannula and supporting strap arrangement that will permit a positive positioning of the cannula against the wearer's nasalabidial area.

It is also an object of the invention to provide a nasal cannula that will permit a positive guiding of the oxygen supply along the natural contours of the nasal passage directly into the pharynx.

It is another object of the invention to provide a flexible nasal cannula which when positioned on the wearer, will spread the pressure over the nasalabidial area where previous cannulas have caused irritation and inflamation.

It is a further object of the invention to provide a nasal cannula that is held on the face in such a manner that the nasal extensions are prevented from rolling out of the nostrils.

It is a further object of the invention to provide a simple, integral nasal cannula that is comfortable to wear.

It is a further object of the invention to provide a nasal cannula assembly that may have the cannula pressed against the nasal septum with a minimal amount of pressure.

It is an additional object of the invention to provide a nasal cannula free from straight edge surfaces that result in pressure points along the nasal septum and nasalabidial area.

DESCRIPTION OF THE DRAWINGS

FIG. 1 is a front elevational view of a cannula assembly according to the present invention in position on a patient;

FIG. 2 is a front elevational view of the novel cannula;

FIG. 3 is an enlarged cross-sectional view taken along lines 3—3 of FIG. 2 showing its relative position when secured to a patient with its extensions inserted into the nasal cavity; and FIG. 4 is a top plan view of the novel cannula.

DESCRIPTION OF THE PREFERRED EMBODIMENT

The novel nasal cannula assembly will now be described by referring to the drawings. In FIG. 1, the cannula assembly, generally designated numeral 10 is illustrated in position on a patient's face. The assembly comprises the nasal cannula 12, a pair of auxiliary oxygen supply tubes 26 and 27 connected to opposite ends of the cannula, a main oxygen supply line 29, a connector 28 for joining auxiliary tubes 26 and 27 to supply tube 29, and a slip loop 31 disposed about auxiliary tubes 26 and 27.

The structure of cannula 12 is best understood by viewing FIGS. 2-4. It is normally fabricated by a dip molding process. The composition of the cannula is preferrably of a thermoplastic composition such as polyvinyl chloride or polyvinyl acetate, which materials are quite pliable or flexible. The cannula is generally a hollow tubular member having an oxygen supply opening at each end. It is of a length sufficient to span the width of an average patient's nostrils. The cannula 12 has a main body portion 13 whose cross-section is oval shaped with a vertical orientation and having a pair of spaced, hollow tubular extensions 14 and 15 integral with and projecting upwardly from the upper surface of the main body portion. The tubular extensions 14 and 15 terminate in gas direction orifices 40, 41 with the hollow portion of the extensions communicating with the hollow main portion. The main body portion 13 has a horizontal axis X extending along its length. Elbows 16 and 17 are formed at each end of the main body portion with arms 18 and 19 extending outwardly therefrom. The arms 18 and 19 have a Y-axis extending along their lengths that intersect the horizontal plane of the X-axis of the main body portion at an acute angle A from above the horizontal plane. The Y-axis extending along the length of each arm also extends rearwardly at an acute angle B to the horizontal axis X of the main body portion 13. At the outer ends of arm portions 18 and 19 are sleeve portions 20 and 21 of a reduced diameter that receive the open ends of the auxiliary supply tubes 26 and 27. These supply tubes are friction fitted or bonded in place therein.

The position of the Y axis relative to the X axis is describable only in a three dimensional sense and must therefore be shown by two figures, these being FIGS. 2 and 4. It can be seen from FIGS. 2 and 4, that, assuming a first plane passes through the X or body axis and passes through the centers of orifices 40 and 41, the Y or arm axis extends both outwardly and upwardly from this plane. If a second plane is now envisioned which is normal the first plane and includes the X axis, the angle B of FIG. 2 is the angle between the Y axis and the normal projection or the Y axis on the second plane and the angle A of FIG. 4 is the angle between the Y axis and the normal projection of the Y axis on the first plane.

FIGS. 1 and 3 illustrate the preferred manner in which the cannula assembly is worn by a patient. The cannula 12 rests across the patient's nasalabidial area and the flexible auxiliary oxygen supply tubes 26 and 27 are directed across the patient's face, over and behind the ears, down the jaw areas and brought together under the chin. A slip loop 31 of sufficient size to encompass both auxiliary supply tubes 26 and 27 may then be adjusted so that the cannula 12 will remain firmly in place without the tubes being unduly taut. The arms 18 and 19 of cannula 12 have a molded in upward acute angle B with rerespect to the horizontal plane of the axis of the main body portion such that the Y-axis of the arm portions, if extended, will pass substantially tangential to the top of the patient's ears. The arms of cannula 12 also have molded into them a rearward acute angle A with respect to the horizontal axis of the main body portion such that the Y-axes of the arm portions, if extended, will also pass substantially tangential to the top of the patient's ears. The above molded in angles of the arm portions 18 and 19 serve to minimize the amount of tension applied upon oxygen supply tubes 26 and 27 to keep the cannula in position against the patient's nasalabidial area when the patient's head is in the upright position. When the patient is in the prone position, the inwardly and upward angles of the cannula arm portion allow it to adapt to the contour of the patient's face allowing only its rounded bottom surface to contact the face with the weight of the cannula being spread across the length of the cannula's arm portions.

The nasal extensions 14 and 15 are shown to be curved in FIG. 3 and they extend into the nasal cavity N. There are no sharp edge openings in the tips of the extensions to irritate the nasal passage due to the continued movements of breathing. Also, the soft, flexible material of the cannula permits it to easily conform to the contours of the nasal cavity. The oxygen supply is therefore guided throughout administration along the normal airways of the nasal cavity directly into the pharynx P. As a result, there is no tendency for oxygen to pass up into the upper reaches of the nasal cavity where it would cause pressure, escape into the cranial cavities or otherwise irritate the patient.

Having thus described the invention, what is claimed as new and useful and is desired to be secured by U.S. Letter Patent is:

1. A nasal cannula assembly designed for contact with the nasalabidial area of a patient's nose and comprising:
    (a) a hollow tubular member having an oxygen supply opening at each end, said tubular member having a central portion of sufficient length to span the width of an average patient's nostrils and end portions extending acutely from each end of said central portion, said central portion having a pair of spaced, hollow tubular extensions integral with and projecting normally therefrom said tubular extensions terminating in gas directing orifices and which hollow portion of said extensions communicate with said hollow main body portion,
    (b) said central portion having a longitudinal axis extending along its length, each said tubular extensions having a longitudinal axis, said longitudinal axis of said central portion and said longitudinal axis of said extensions lying in a first plane each said end portions of said tubular member having a longitudinal axis lying in a second plane, said longitudinal axis of said central portion also lying in a third plane perpendicular to said first plane, each said end portion longitudinal axis lying in said second plane and projecting from said first and third planes at an acute angle greater than zero, said orifices of said tubular extensions angled acutely from said first plane toward said second plane.

2. A nasal cannula assembly as recited in claim 1, wherein the acute angles at which the axes of the end portions intersect the first and second planes is such that the end portions, if extended, will pass substantially tangential to the top of the patient's ear.

3. A nasal cannula assembly as recited in claim 2, wherein said end portions have at their outer ends, sleeve portions of reduced diameter for receiving a flexible oxygen supply tube.

4. A nasal cannula assembly as recited in claim 3, wherein said tubular extensions terminating in orifices are curved.

5. A nasal cannula assembly as recited in claim 4, wherein said tubular member is composed of a material suficiently flexible to conform to the surface contour of the patient's body.

6. A nasal cannula assembly as recited in claim 5, wherein said main body portion has a cross-section that is oval-shaped with the major axis parallel to said first plane.

7. A nasal cannular assembly as recited in claim 2, wherein said main body portion has a cross-section that is ovalshaped with the major axis parallel to said first plane.

8. A nasal cannular assembly as recited in claim 1, wherein said main body portion has a cross-section that is oval-shaped with the major axis parallel to said first plane.

* * * * *